United States Patent
Kim et al.

(10) Patent No.: US 11,234,903 B2
(45) Date of Patent: Feb. 1, 2022

(54) METHODS FOR ENHANCING OPTICAL AND STRENGTH PROPERTIES IN CERAMIC BODIES HAVING APPLICATIONS IN DENTAL RESTORATIONS

(71) Applicant: James R. Glidewell Dental Ceramics, Inc., Newport Beach, CA (US)

(72) Inventors: Jae Won Kim, Irvine, CA (US); Akash, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 96 days.

(21) Appl. No.: 16/859,132

(22) Filed: Apr. 27, 2020

(65) Prior Publication Data

US 2020/0261322 A1 Aug. 20, 2020

Related U.S. Application Data

(62) Division of application No. 15/923,565, filed on Mar. 16, 2018, now Pat. No. 10,667,992.

(51) Int. Cl.
| | |
|---|---|
| *A61K 6/78* | (2020.01) |
| *C04B 41/00* | (2006.01) |
| *C04B 41/51* | (2006.01) |
| *C04B 41/50* | (2006.01) |
| *C04B 41/88* | (2006.01) |

(Continued)

(52) U.S. Cl.
CPC .............. *A61K 6/78* (2020.01); *A61K 6/818* (2020.01); *A61K 6/822* (2020.01); *B05D 1/28* (2013.01); *B05D 3/0272* (2013.01); *C04B 41/009* (2013.01); *C04B 41/5012* (2013.01); *C04B 41/515* (2013.01); *C04B 41/52* (2013.01); *C04B 41/88* (2013.01); *C04B 41/89* (2013.01); *C04B 2111/00836* (2013.01); *C04B 2111/80* (2013.01)

(58) Field of Classification Search
CPC .......... A61K 6/818; C04B 2111/00836; C04B 35/48; C04B 35/486; C04B 35/482
See application file for complete search history.

(56) References Cited

U.S. PATENT DOCUMENTS

| | | | |
|---|---|---|---|
| 3,875,391 | A | 4/1975 | Hamling |
| 4,557,691 | A | 12/1985 | Martin et al. |

(Continued)

FOREIGN PATENT DOCUMENTS

| | | |
|---|---|---|
| WO | 2009014903 A2 | 1/2009 |
| WO | 2010107678 A1 | 9/2010 |

(Continued)

OTHER PUBLICATIONS

Wikipedia, Yttria-stabilized zirconia, https://en.wikipedia.org/wiki/Yttria-stabilied_zirconia, printed Apr. 15, 2019, in 4 pages.

*Primary Examiner* — Noah S Wiese
(74) *Attorney, Agent, or Firm* — Charles Fowler

(57) ABSTRACT

A method for enhancing optical properties of sintered, zirconia ceramic bodies and zirconia ceramic dental restorations is provided. The porous or pre-sintered stage of a ceramic body is treated with two different yttrium-containing compositions and sintered, resulting in sintered ceramic bodies having enhanced optical properties. The enhanced optical properties may be substantially permanent, remaining for the useful life of the sintered ceramic body.

4 Claims, 6 Drawing Sheets

Related U.S. Application Data

(60) Provisional application No. 62/472,100, filed on Mar. 16, 2017, provisional application No. 62/472,195, filed on Mar. 16, 2017.

(51) Int. Cl.

| | | |
|---|---|---|
| *C04B 41/52* | (2006.01) | |
| *C04B 41/89* | (2006.01) | |
| *A61K 6/818* | (2020.01) | |
| *A61K 6/822* | (2020.01) | |
| *B05D 1/28* | (2006.01) | |
| *B05D 3/02* | (2006.01) | |
| *C04B 111/80* | (2006.01) | |
| *C04B 111/00* | (2006.01) | |

(56) References Cited

U.S. PATENT DOCUMENTS

| | | |
|---|---|---|
| 6,709,694 B1 | 3/2004 | Suttor et al. |
| 6,908,872 B2 | 6/2005 | Tanaka et al. |
| 8,298,329 B2 | 10/2012 | Knapp et al. |
| 8,696,954 B2 | 4/2014 | Tanaka |
| 8,697,176 B2 | 4/2014 | Wang et al. |
| 8,835,004 B2 | 9/2014 | Dittmann et al. |
| 8,936,848 B2 | 1/2015 | Jung et al. |
| 9,095,403 B2 | 8/2015 | Carden et al. |
| 9,155,597 B2 * | 10/2015 | Brodkin .................. A61K 6/884 |
| 9,212,065 B2 | 12/2015 | Kamada et al. |
| 9,365,459 B2 | 6/2016 | Carden et al. |
| 9,434,651 B2 | 9/2016 | Carden |
| D769,449 S | 10/2016 | Leeson et al. |
| 9,512,317 B2 | 12/2016 | Carden et al. |
| 9,554,881 B2 | 1/2017 | Wang et al. |
| 9,592,105 B2 | 3/2017 | Hauptmann et al. |
| 9,597,265 B2 | 3/2017 | Carden et al. |
| 9,872,746 B2 | 1/2018 | Hauptmann et al. |
| 10,034,728 B2 | 7/2018 | Jung et al. |
| 2010/0221683 A1 | 9/2010 | Franke et al. |
| 2014/0101869 A1 | 4/2014 | Carden et al. |
| 2015/0079408 A1 | 3/2015 | Piascik et al. |
| 2016/0002112 A1 | 1/2016 | Stephan |
| 2016/0368826 A1 * | 12/2016 | Calado Da Silva .. C04B 35/486 |
| 2018/0265420 A1 | 9/2018 | Kim et al. |

FOREIGN PATENT DOCUMENTS

| | | |
|---|---|---|
| WO | 2013170705 A1 | 11/2013 |
| WO | 2014022643 A1 | 6/2014 |

* cited by examiner

METHODS FOR ENHANCING OPTICAL AND STRENGTH PROPERTIES IN CERAMIC BODIES HAVING APPLICATIONS IN DENTAL RESTORATIONS

RELATED APPLICATIONS

This application is a divisional application of U.S. patent application Ser. No. 15/923,565, filed on Mar. 16, 2018, which claims the benefit of, and priority to, U.S. Provisional Patent Application No. 62/472,100, filed Mar. 16, 2017, and U.S. Provisional Patent Application No. 62/472,195, filed Mar. 16, 2017, the entireties of which applications are incorporated herein by reference.

BACKGROUND

Ceramic bodies colorized by known processes before or after sintering, show a decrease in translucency upon application of a colorant. In dental applications, pre-sintering or post-sintering colorization techniques compete to balance hue, chroma, value and translucency inherent in the structure of natural dentition. For example, techniques to create an enamel effect may reduce the overall translucency of the restoration. Moreover, pre-sintering treatments applied to enhance optical properties may result in a decrease in strength or cracking. Furthermore, post-sintering treatments to enhance or mimic a translucent effect are often temporary, failing to last the useful life of the restoration.

SUMMARY

A method for enhancing optical properties of sintered, zirconia ceramic bodies and zirconia ceramic dental restorations is provided. A method is provided for treating the porous or pre-sintered stage of a ceramic body to enhance optical properties of the ceramic body after sintering. The methods provide enhanced optical properties that may be substantially permanent, remaining for the useful life of the sintered ceramic body.

Method steps comprise a) applying a first yttrium-containing composition onto a surface of a pre-sintered or porous ceramic body; b) applying a second yttrium-containing composition onto the pre-sintered or porous ceramic body; and c) sintering the ceramic body.

A first yttrium-containing composition may be an aqueous liquid comprising an yttrium-containing component, and optionally, a colorant to achieve desired color or shade properties of the final sintered body. The second yttrium-containing composition may be an aqueous liquid comprising an yttrium-containing component, and optionally, a colorant; the second yttrium-containing composition may comprise a greater concentration of yttrium than the first yttrium-containing composition. Optionally, a solubility enhancing agent, such as citric acid, may be provided to enhance the solubility of the yttrium-containing component. In dental restoration applications, additional components may be added to the yttrium-containing compositions to impart an enamel illusion effect. In an embodiment, the incisal region of the restoration may have enhanced translucency and a blue to gray hue that resembles a natural translucent incisal enamel area of natural dentition that is unsupported by dentin. Optionally, an additional component for imparting a pink hue may be provided to the restoration. Both first and second compositions may be aqueous solutions, or aqueous mixtures in which at least a portion of the yttrium-containing component is in solution.

Translucency of sintered ceramic bodies that have been treated with the yttrium-containing compositions is enhanced, compared to the translucency of untreated sintered ceramic bodies. Final restorations may be formed that exhibit a translucency gradient having a higher translucency at the incisal edge or adjacent the edge of an occlusal that decreases from incisal region to cervical, or margin, region.

L*a*b values within a desired range of bleached or natural tooth shades for finished ceramic dental restorations is achieved. A detectable ΔE for color space may be imparted along vertical axes of a restoration providing a polychromatic effect. In some embodiments, restorations may be formed having higher L values (CIE Color Space) on the facial surface in the incisal region than in a middle-region (between the incisal region and cervical region) of a restoration.

The final restorations have biaxial strength and/or three-point bend strength suitable anterior or posterior dental applications. Dental restorations made according the methods described herein may, optionally, have a fracture toughness gradient increase from incisal region to cervical or margin region, when tested according to the method disclosed herein. Dental restoration applications include single units, such as crowns, or multi-unit restorations, such as bridges.

DETAILED DESCRIPTION

Figure 1:
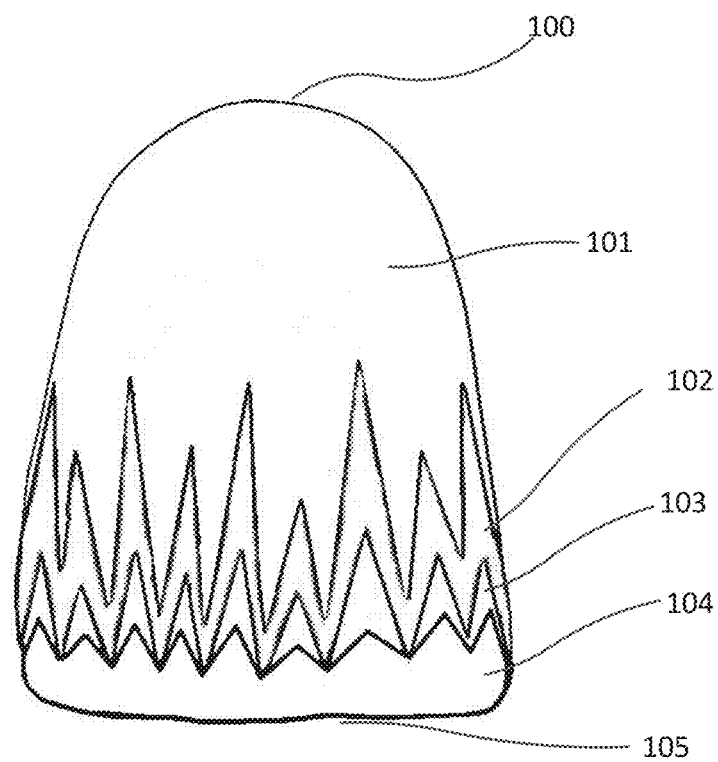
FIG. 1 is an illustration of a method of making a dental restoration according to one embodiment.
Figure 2:
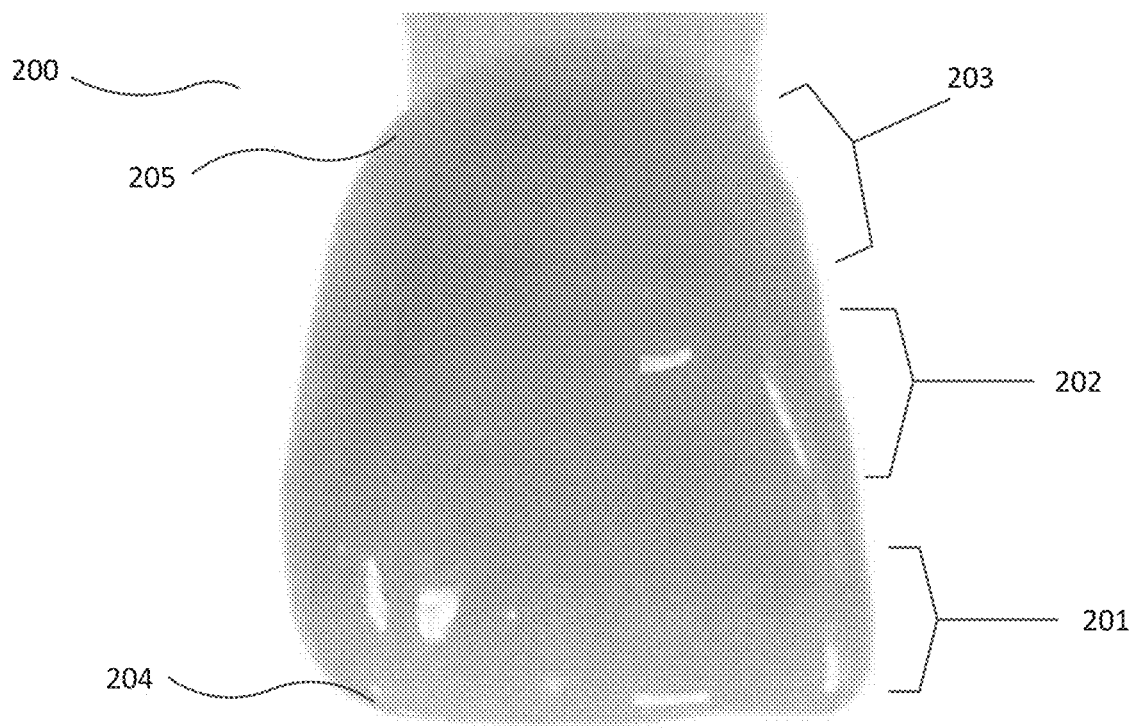
FIG. 2 is a photograph of a sintered zirconia dental restoration prepared according to one embodiment.

A method for making sintered ceramic bodies having enhanced optical properties suitable for use as dental restorations, is provided. With reference to FIG. 1, the method comprises the steps of treating a pre-sintered or porous ceramic body (100), by applying a first yttrium-containing composition (101), and applying a second yttrium-containing composition (102) onto the pre-sintered or porous ceramic body, then sintering the ceramic body to form a sintered body. A sintered dental restoration in the shape of a tooth (FIG. 2, at 200), made by these methods may comprise a translucency gradient (201, 202, 203) between incisal edge (or edge of occlusal surface) (204) in the apical direction toward the margin (205) edge with decreasing translucency as the distance from the incisal edge (204) increases.

First and second yttrium-containing compositions may be liquids, for example, in the form of mixtures or solutions. A first yttrium-containing composition comprises: an yttrium-containing component, and optionally, a colorant to achieve desired shade properties. A second yttrium-containing composition may have a greater concentration of yttrium than the first yttrium-containing composition, and optionally, comprises a colorant. Optionally, a solubility enhancing agent may be used to enhance the solubility of the yttrium-containing component, such as citric acid, and an optional component to enhance an enamel effect.

The yttrium-containing component may be the same or different component in the first and second yttrium-containing compositions, and may comprise an yttrium salt, including but not limited to salts such as yttrium chloride, including yttrium chloride hexahydrate (e.g., yttrium (III) chloride hexahydrate), yttrium nitrate (e.g., yttrium (III) nitrate hexahydrate), and yttrium carbonate (yttrium (III) carbonate hydrate). The yttrium-containing component may be in a solvent such as water, inorganic solvents, or organic solvents, or mixtures thereof. The solvent is present in an amount suitable for dissolving or solubilizing the yttrium-containing composition to achieve a desired concentration in solution.

The first yttrium-containing composition may comprise less than approximately 40 wt % yttrium salt in an aqueous solution based on the total weight of the first yttrium-containing composition. Alternately, a first yttrium-containing composition may comprise an amount between 5 wt % and 35 wt % yttrium salt in solution, or an amount between 5 wt % and 20 wt % yttrium salt in solution, or an amount between 5 wt % and 15 wt % yttrium salt in solution, or in an amount between 10 wt % and 20 wt % yttrium salt in solution, or an amount between 10 wt % and 15 wt % yttrium salt in solution, based on the total weight of the first composition. The first yttrium-containing composition may have a lower concentration of yttrium or of an yttrium-containing component in solution than the second yttrium-containing composition. In one embodiment, the first yttrium-containing composition comprises between 5 wt % and 30 wt % yttrium chloride as yttrium (III) chloride hexahydrate.

The second yttrium-containing composition may comprise yttrium salt in an amount between approximately 10 wt % and 70 wt % in solution, based on the total weight of the second yttrium-containing composition. In other embodiments, the second composition comprises between approximately 20 wt % and 70 wt % yttrium salt in solution, or between approximately 30 wt % and 70 wt % yttrium salt in solution, or an amount from approximately 40 wt % to approximately 70 wt % in solution, or an amount from approximately 40 wt % to approximately 65 wt %, or an amount from approximately 50 wt % to approximately 67 wt % in solution, or in an amount from approximately 50 wt % to approximately 70 wt %, based on the weight of the second yttrium-containing composition.

A solubility enhancing agent may be used to increase solubility of the yttrium-containing agent. For example, in one embodiment, the second yttrium-containing composition comprises between approximately 45 wt % and approximately 70 wt % yttrium chloride (based on the total weight of the second yttrium-containing composition) solubilized in an aqueous solution comprising between 0.5M and 2M citric acid. In one embodiment, the first yttrium-containing composition comprises an amount between 5 wt % and 30 wt % of yttrium chloride (as yttrium (III) chloride hexahydrate), and the second yttrium-containing composition comprises greater than 30 wt % yttrium chloride.

An enamel-effect agent may be added to the first or second yttrium-containing composition to increase a blue or gray hue in the incisal area of a sintered ceramic body. Enamel-effect agents include, but are not limited to materials such as a copper-containing or cobalt-containing component; additionally, a coloring agent such as an erbium-containing composition, may be added to provide a pink color. The weight percent of a cobalt-containing component in the yttrium-containing compositions, such as a cobalt salt, cobalt chloride or cobalt nitrate, may be in the range of approximately 0.005 wt. % to approximately 0.3 wt. %, or approximately 0.01 wt. % to approximately 0.2 wt. %, or approximately 0.01 wt. % to approximately 0.15 wt. %, or approximately 0.04 wt. % to approximately 0.1 wt. %, or approximately 0.04 wt. % to approximately 0.08 wt. %, or approximately 0.15 wt. % to approximately 0.3 wt. %, based on the total weight of the second yttrium-containing composition.

The first, and optionally, second, yttrium-containing composition further comprise a colorant to provide a dental restoration with a shade that is in the range of natural dentition, or a specific target for chroma, hue, and/or value, for example as measured by color space analysis (e.g. L*a*b values). By methods provided herein, a natural tooth shade or bleached shade, such as a shade based on a Vita Classic Shade Guide or Bleached Shade, may be attained in the final sintered body. Examples of colorants, coloring agents and/or coloring liquids suitable for use herein may include those described in commonly owned U.S. Pat. No. 9,095,403, which is hereby incorporated by reference in its entirety, herein.

Colorants may comprise at least one coloring agent comprising a metal-containing component, including metal compounds or complexes, such as a metallic salt or metal oxide. Metal-containing components may comprise metallic salts of transition metals from groups 3-14 on the periodic table, metallic salts of rare earth metals, and metal-containing components in the forms of oxides or containing anions such as $Cl^-$, $SO_4^{2-}$, $SO_3^{2-}$, $Br^-$, $F^-$, $NO_2^-$, and $NO_3^-$, may be suitable for use in the methods described herein. Examples of coloring agents suitable for use herein include, but are not limited to, salts or oxides of metals such as iron, terbium, erbium, chromium, cobalt and manganese.

Coloring agents disclosed in commonly owned US Patent Publication Nos. U.S. Pat. Nos. 9,095,403, 9,365,459, and 9,512,317, each of which is incorporated by reference herein in their entirety, may be suitable for use herein. In one embodiment, the coloring agent comprises at least one metallic salt or oxide of the metals selected from chromium, terbium and manganese. Terbium may be present, for example, as terbium chloride, chromium as chromium chloride, and manganese as manganese sulfate.

The selection of coloring agents added to the yttrium-containing compositions, as well as the selection of the amount or concentration, to provide a target shade in a final sintered body, may be dependent on the initial shade of the bisque ceramic to which the first yttrium containing composition is applied. For example, higher weight percentages of coloring agent may be added to achieve a specific target shade in a final sintered ceramic body (e.g., such as A2 Vita Classic shade), where the first yttrium-containing composition is applied to an unshaded pre-sintered ceramic rather than a shaded pre-sintered ceramic.

In some embodiments, a coloring agent in the form of a metal salt is selected in the range of approximately 0.01 wt % to approximately 5 wt % metallic salt based on the total weight of the first yttrium-containing composition, or approximately 0.05 wt % to approximately 2 wt % metallic salt, or approximately 0.07 wt % to approximately 1.5 wt %, or approximately 0.05 wt % to approximately 2 wt % metallic salt based on the total weight of the first yttrium-containing composition. Alternatively, the amount of metallic salt is in a range of approximately 0.1 to 0.5 wt % metallic salt based on the total weight of the first yttrium-containing composition. In some embodiments, a coloring agent in the form of a metallic salt is selected in the range of approximately 0.001 wt % to approximately 0.5 wt % metallic salt based on the total weight of the second yttrium-containing composition. Coloring liquids to be incorporated into yttrium-containing compositions may be prepared as aqueous coloring solutions having no solid colorant particles that are detectable at ambient temperature to the unaided eye after mixing a coloring agent with a solvent. Multiple coloring liquids may be used in combination with the yttrium-containing compositions for application on shaded or unshaded bisque ceramic materials to impart a range of natural or bleached tooth shades. Prepared coloring liquids applied to a porous unshaded or shaded zirconia ceramic result in sintered restorations that matches, for example, a Vita shade such as BL1, BL2, BL3, and BL4 (bleach shades) and shades A1-D4 shades (e.g. A1, A2, A3, A3.5, A4, B1, B2, B3, B4, C1, C2, C3, C4, D2, D3, and D4) from Vita Classical shade guide. Additionally, colorants, such as organic markers may be added to either yttrium-containing composition.

Optionally, solubility enhancing agents including acids, such as citric acid, may be added in an amount to increase the solubility of the colorant or yttrium-containing component. For example, an aqueous yttrium-containing composition solution may comprise approximately 0.05M to approximately 5M citric acid solution where the concentration of yttrium-containing agent is greater than, for example approximately 45 wt. % of the total yttrium-containing composition. In other embodiments, the yttrium-containing composition may comprise 0.5M to 5M citric acid, or 0.5 to 2M citric acid, or 1M to 2M citric acid solution. Organic solvent or non-organic solvent may also be included in the coloring liquid or the yttrium-containing composition, for example, to increase solubility of the components, such as the coloring agents and yttrium-containing component, to aid in solubility reducing or eliminating visible particles of colorant or the yttrium-containing.

Yttrium-containing compositions, when applied to green or pre-sintered ceramic bodies that have retained porosity, may penetrate into the porous network. Ceramic bodies comprise ceramic materials that include, but are not limited to alumina, zirconia, such as stabilized zirconia, including yttria-stabilized tetragonal zirconia, and mixtures thereof. Ceramic green bodies may be partially consolidated, and like bisque or pre-sintered bodies, have a density below full theoretical density of the ceramic sintered form.

Examples of stabilized zirconia suitable for use herein include commercially available yttria-stabilized zirconia commercially available from Tosoh USA, yttria-stabilized or partially-stabilized zirconia that has been stabilized with approximately 0.1 mol % to approximately 8 mol % yttria, or approximately 2 mol % to approximately 7 mol % yttria, or from approximately 2 mol % to approximately 5 mol % yttria, or from approximately 2 mol % to approximately 4 mol % yttria. In one embodiment, dental restoration forms comprise approximately2 mol % to approximately 3 mol % yttria-stabilized zirconia ceramic material.

Ceramic material may comprise approximately 85 wt % to approximately 100 wt % zirconia ceramic material, and, optionally, minor amounts of other materials such as alumina. Zirconia ceramic bodies may be made from ceramic materials that comprise approximately 85 wt % to approximately 98 wt % zirconia or stabilized zirconia, based on the total weight of the zirconia ceramic material, or approximately 85 wt % or greater, or approximately 90 wt % or greater, or approximately 95 wt % or greater, or more than approximately 97 wt % or greater zirconia or stabilized zirconia, based on the total weight of the zirconia ceramic material.

Zirconia ceramic materials may comprise zirconia powder having a substantially uniform particle size distribution, such as powder with an average size in a range from approximately 0.005 micron ($\mu$m) to approximately 1 $\mu$m, or approximately 0.05 $\mu$m to approximately Examples of ceramic material suitable for use herein also include zirconia described in commonly owned U.S. Pat. No. 8,298,329, which is hereby incorporated by reference in its entirety.

Green stage ceramic bodies may be formed from shaded or unshaded ceramic material. Natural unshaded zirconia powder may have a white appearance. Alternatively, pre-shaded ceramic materials that are shaded to match a target or desired shade in a sintered body may be pressed, or otherwise shaped, into shaded porous ceramic bodies for use herein that include commercially available ceramic blocks including, but not limited to millable blocks sold under the name BruxZir® (e.g., BruxZir® Shaded 16 series in target shades matching VITA Classic shades (Glidewell Laboratories, Irvine, Calif.)).

A porous or pre-sintered ceramic body may be shaped as a block, disk, near net shape, or a preform that approximates the size and/or shape of a single or multi-unit dental restoration, such as a crown, on-lay, bridge, or partial or full solid-body denture. Ceramic bodies may be made by known processes for pressing, slip casting, and automated processes, including additive (e.g., 3-D printing) and subtractive (e.g., milling) automated processes. Processes for making ceramic bodies suitable for use herein include those described in commonly owned U.S. Pat. Nos. 9,365,459, 9,434,651, and 9,512,317, all of which are hereby incorporated in their entirety, herein. Commercially available pre-sintered or bisque state ceramic bodies include those that have been heated to increase the density of a green body to below the full theoretical density of a fully sintered ceramic body in accordance with suggestions provided by the manufacturer. Pre-sintered ceramic bodies include those having a density of approximately 30% to 90%, or approximately 50% to 90% of full theoretical density of the sintered ceramic body, while maintaining porosity sufficient for penetration of yttrium-containing compositions.

A bisque stage ceramic body may be shaped in the form of a dental restoration, such as a single unit crown, based on the individual requirements of a patient, by milling or automated processes, including CAD and/or CAM processes, prior to application of the yttrium-containing composition. Alternatively, after application of the first and second yttrium-containing compositions, the ceramic material may be sintered prior to milling into a dental restoration by making a ceramic preform having a size and shape that accommodates most custom restorations. Examples of suitable shaped forms which may be sintered to full theoretical density prior to shaping may be found in commonly owned U.S. Patent Publication No. 2013/0316305, and U.S. Pat. No. D769, 449, both of which are hereby incorporated herein in their entirety.

One or more applications of the first yttrium-containing composition may be applied to infiltrate, absorb or penetrate a porous pre-sintered ceramic body. Methods described herein include applying the first yttrium-containing composition to all or a portion of a porous or pre-sintered ceramic body by one or more techniques, including but not limited to dipping, dripping, spraying, or painting, for example with a brush or pen tip. The entire ceramic body may be submerged in the first composition for sufficient time to penetrate the entire thickness of all or a portion of the ceramic body. In another embodiment, the first yttrium-containing composition applied to one surface of a tooth-shaped ceramic body (e.g., buccal surface), may penetrate through the thickness of the ceramic body to wet a second surface (e.g., lingual surface), without direct application onto that second surface. In other embodiments, a light spray or brush coating of the first yttrium-containing composition onto one or more surfaces of a bisque stage ceramic body only partially penetrates the thickness of the ceramic body. In a further embodiment, a first yttrium-containing composition applied drop-wise to a cavity or concave surface of may penetrate partially or fully through the thickness of a ceramic body shaped as a dental restoration crown or preform body. In one embodiment, the second yttrium-containing composition is applied to a portion of the porous ceramic body that contains the first yttrium-containing composition. Where the first and second yttrium-containing compositions are present in the same portion of the porous ceramic body, the liquid first and second yttrium-containing compositions may mix or blend, for example, at the edge of the second yttrium-containing composition and may form a gradient.

Figure 3:
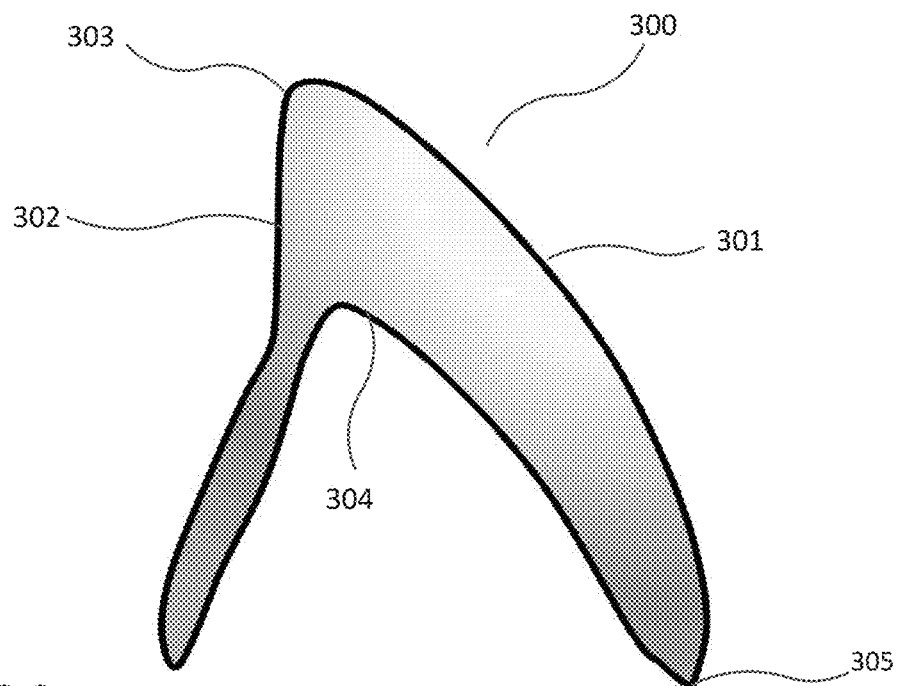
FIG. 3 is an illustration of a cross-sectional representation of a dental restoration according to one embodiment.
Figure 4:
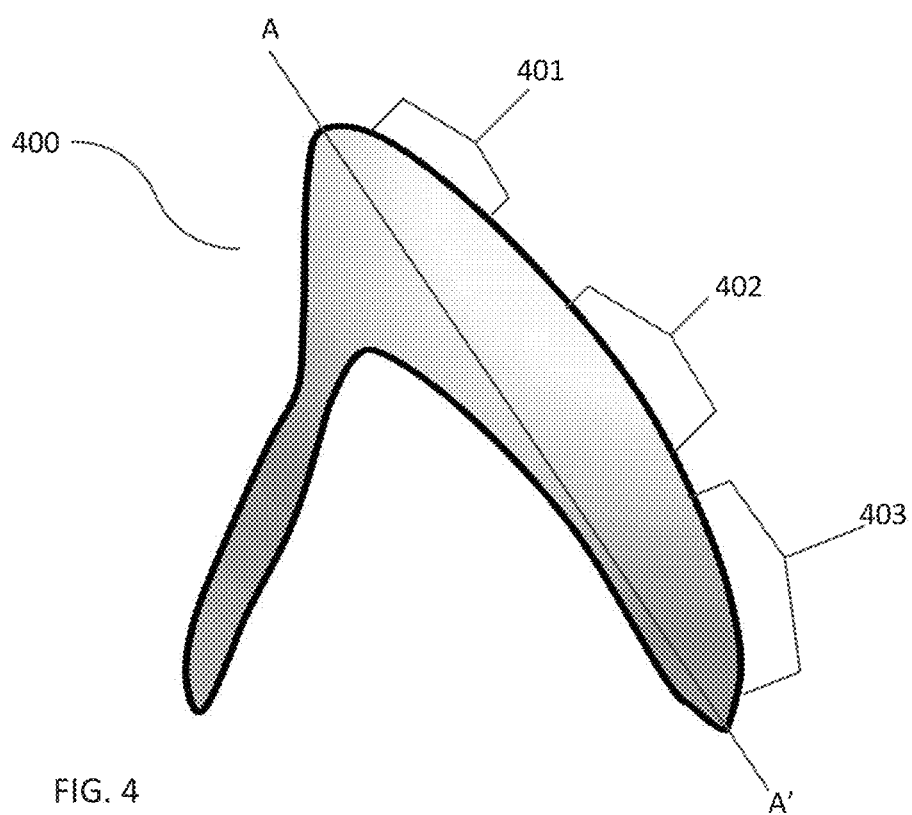
FIG. 4 is an illustration of a cross-sectional representation of a dental restoration according to one embodiment.

With reference to the cross-sectional representation of a ceramic body shaped as a dental restoration (300, 400) of FIG. 3 and FIG. 4, a first yttrium-containing composition may be applied to one or more external surface (e.g., buccal/labia surface, which may be referred to as a facial surface herein for convenience) (301), lingual (302), distal, mesial, incisal or occlusal (biting) surfaces or edges (303). Optionally, the first yttrium-containing composition may be applied to an internal surface (304) or cavity surface, such as a surface that abuts a tooth preparation or implant abutment for installation in the mouth of a patient. Upon application to the internal surface or cavity surface (304), the yttrium-containing composition may diffuse partially through the thickness of the ceramic dental restoration body, or it may penetrate the entire thickness of the ceramic dental restoration body, for example, to wet the facial surface (i.e., buccal/labial) (301) and/or lingual surface (302), at an incisal region (e.g., up to about one third of the length of a restoration adjacent the incisal edge) and/or a middle region (approximately the middle third of the restoration.)

In one embodiment of this method, the first yttrium containing composition is applied from incisal or occlusal edge (303) to approximately one-third (the incisal third) or approximately two-thirds (the middle third) of the length of the restoration beyond the incisal edge toward the margin (305) by direct application onto the surface, or by diffusion from the incisal edge (303) toward the margin (305). Multiple applications of the first yttrium-containing composition may be applied to the ceramic body before the first application completely dries.

At least one application of the second yttrium-containing composition (102, 103, and 104) may be applied to a tooth-shaped ceramic body (100) over the first yttrium-containing composition (101) before the applied first yttrium-containing composition dries. As exemplified in FIG. 1, the second yttrium-containing composition may be applied to an incisal or occlusal surface (biting surface), or along the incisal or occlusal edges (105), or applied to both the biting surface and along the edge between mesial and distal restoration tooth edges. In one embodiment, the second yttrium-containing composition is applied to a portion of the porous ceramic body that comprises the first yttrium-containing composition before the aqueous or liquid component of the first yttria-containing composition is removed (e.g., by evaporation or heating). The second yttrium-containing composition may be applied to provide an yttrium-enhanced area (e.g., 102) that extends from the biting edge direction for a distance of approximately 0.5 mm to approximately 5 mm, or approximately 0.5 mm to approximately 6 mm from the biting edge (105) on the facial surface (i.e., buccal or labial surface) toward the cervical region, extending between the mesial and distal edges of the tooth. In other embodiments, an yttrium-enhanced area (e.g., 103) comprises an area for a distance of approximately 0.5 mm to approximately 3 mm from the biting edge (occlusal or incisal edge, 105) toward the cervical region and extending mesial-distally. In one embodiment, second and subsequent applications (e.g., 103 or 104) of the second yttrium-containing composition are applied to at least a portion of the first application (e.g., 102) increasing the amount of yttrium-containing composition in the covered area. The second yttrium-containing composition also may be applied at the biting edge for a distance of, approximately 0.5 mm to approximately 5 mm, or approximately 0.5 mm to approximately 4 mm, or approximately 0.5 mm to approximately 3 mm, or approximately 1 mm to approximately 5 mm, or approximately 1 mm to approximately 3 mm, or approximately 1 mm to 2 mm, beyond the biting (incisal or occlusal) edge (105) toward the cervical region to provide an yttrium enhanced area that extends.

In one embodiment, a method comprises a first step of dipping a porous, pre-sintered zirconia ceramic body in the form of a dental restoration in a first yttrium-containing composition to coat the entire external (buccal and/or lingual) surface, and optionally, internal or cavity (304) surface; a second step of applying one or more coats of the second yttrium-containing composition to an incisal edge or incisal surface area penetrated by the first yttrium-containing composition prior to the first yttrium-containing composition drying. In one embodiment, neither the first or second yttrium-containing compositions are applied at or adjacent (within about 1 mm to 3 mm) a crown margin or cervical region), where enhanced optical properties are not readily apparent when installed in the mouth of a user. The composition may be applied, for example, by spraying or painting, for example, using a brush or pen tip. In one application method, the first and/or second yttrium-containing compositions may be applied (e.g. by brush or pen) to form even or uneven patterns, for example, and may be applied to have a jagged or zigzag edge, as exemplified in FIG. 1. Where the second yttrium-containing composition is applied before the first yttrium-containing composition dries, the compositions that have penetrated the porous ceramic body may blend or mix at zigzag or jagged edges of the second yttrium-containing composition, creating a gradual transition between sequential, adjacent applications.

In another embodiment, pre-sintered ceramic bodies shaped as pre-forms or near net shapes may also be treated with the yttrium-containing compositions. In one embodiment, the pre-form or near net shape may be dipped in a first yttrium-containing composition to achieve partial or complete penetration through the thickness of a bisque stage ceramic preform body. In another embodiment, the first yttrium-containing composition may be applied to one or more sides or surfaces of a ceramic pre-form or near net shape that corresponds with an occlusal or buccal surface of a restoration that is ultimately milled from the ceramic body. One or more applications of the second yttrium-containing composition may be applied to the preform or near net shape ceramic body over the first yttrium-containing composition the side or surface that corresponds with an occlusal or buccal tooth surface, before the applied first yttrium-containing composition dries. In this application, the treated pre-form may be sintered to full theoretical density prior to milling or grinding into a patient-specific dental restoration.

In some embodiments, a gradient of either the first or second yttrium-containing compositions, or both, is formed by diffusion through a portion of a ceramic body. The gradient may comprise increasing concentrations of yttrium-containing component, coloring agent and/or enamel enhancing agent within the ceramic body as the distance from the application sight decreases. Upon sintering, the sintered body may comprise gradients of the sintered form of the yttrium-containing component, the coloring agent, and/or the cobalt-containing component, resulting in gradients of translucency or strength.

The sintered ceramic body dental restoration (400) exemplified in FIG. 4 has an yttria concentration gradient that decreases in one or more directions from the incisal region (401) toward the cervical region (403). For example, a first yttria concentration gradient (along vertical axis A-A') may decrease from a first concentration at an incisal (or occlusal) edge (303) or incisal region (401) to a second (or, e.g., a third) lower yttria concentration at a second region (402) at a greater distance from the incisal edge than the incisal region (401). The yttria concentration may be lower at an cervical region (403) (e.g., in a crown margin area than the yttria concentration at either the incisal region (401) or the second region (402) that is between the incisal region (401) and cervical region (403) in the sintered body.

Upon sintering, a translucency gradient may appear for a portion of the restoration surface between incisal edge and cervical region. Multiple translucency values may be measured, for example, at increasing distances from the incisal edge. A ceramic body may have a first translucency value (measured as percent transmittance) in a first region (e.g., incisal region (401)) near the incisal edge, and a second translucency value that is lower than the first value when measured, for example, at a second region (402) that is at a greater distance from the incisal edge. Optionally, the ceramic body may have a third region (e.g., an cervical region (403)) having a third translucency value that is lower than either or both of the first or the second regions, wherein the third region is a greater distance from the incisal edge than either the first or second regions. In this embodiment, a gradient is formed with no distinctly observable transition line(s) observable with the unaided eye between regions having different transmittance values.

In some embodiments, treated zirconia ceramic bodies have higher translucency than untreated zirconia ceramic bodies while maintaining similar L values (based on measured L*a*b values) in the final sintered body. Where translucency is measured as percent transmittance (measured at 700 nm on a 1 mm sample) a treated zirconia ceramic body may have a percent transmittance greater than 40, greater than 41, greater than 43, greater than 45 greater than 47, greater than 49, greater than 50, or greater than 52 percent when measured according to the methods described herein. In one embodiment, the difference between the measured percent transmittance of treated sintered zirconia bodies and the measured percent transmittance of untreated sintered zirconia bodies (similarly prepared from equivalent ceramic materials), is greater than 2% transmittance, or greater than 3%, or greater than 4%, or greater than 5%, or greater than 7%, or greater than 9%, or greater than 10% (corrected for thickness; at 700 nm for a 1 mm thick sample).

In one specific embodiment, a sintered ceramic body made from 3 mol % yttria-stabilized, shaded zirconia treated with first and second yttrium containing compositions (having a color match comparable to an A2 Vita Classic shade) has greater than 47% transmittance at 700 nm for a 1 mm thick sample. Optionally, the sintered body has an L value (CIE Color Space) greater than approximately 65. In a further embodiment, a treated ceramic body having a percent transmittance greater than 40% (at 700 nm for a 1 mm sample,) and an L value greater than 65, has a percent transmittance that is at least a two percentage points greater than an untreated zirconia ceramic body, and less than 1 percent difference in L values than the untreated zirconia ceramic body.

Sintered zirconia ceramic bodies made according to the methods described herein have a biaxial strength, flexural strength, or both biaxial and flexural strength values greater than 500 MPA, or greater than 600 MPA, or greater than 700 MPA, or greater than 800 MPA, or greater than 900 MPA.

A method is provided for imparting enhanced optical properties to a dental restoration comprising the steps of applying a first yttrium-containing aqueous solution comprising at least one metallic salt as a coloring agent, approximately 5 wt. % to approximately 20 wt. % yttrium chloride in water, to a porous dental restoration form comprised of a shaded, white or unshaded porous zirconia ceramic body comprising stabilized with approximately 1 mol % to approximately 8 mol % yttria; applying a second yttrium-containing aqueous solution comprising approximately 40 wt % to approximately 70 wt % yttrium chloride, and approximately 0.04 wt. % to approximately 1.0 wt. % cobalt-containing component, and, optionally, a concentration of citric acid in the range of approximately 0.5M to approximately 1.5M, and optionally, a colorant in additional to cobalt, to a portion of the dental restoration form on to which the first mixture is applied; and after drying the first and second compositions, sintering the treated dental restoration form to a zirconia ceramic body to fully densify the ceramic body, forming a fully formed dental restoration.

In a further embodiment, a method of enhancing optical properties in a dental restoration is provided that comprises obtaining a first aqueous yttrium-containing composition comprising between 5 wt % and 35 wt % of yttrium-containing material based on the total weight of the first aqueous yttrium-containing composition, and a first colorant comprising at least one metal-containing component as a coloring agent; obtaining a second aqueous yttrium-containing composition comprising between 20 wt % and 70 wt % of yttrium-containing material based on the total weight of the second aqueous yttrium-containing composition, wherein the weight percent of yttrium-containing material in the second composition is greater than in the first aqueous yttrium-containing composition, and optionally, a second colorant comprising at least one metal-containing component as a coloring agent; applying the first aqueous yttrium-containing composition to penetrate at least a portion of a porous zirconia ceramic body that is in the shape of a dental restoration; applying the second aqueous yttrium-containing composition to penetrate the incisal region; and sintering the porous zirconia ceramic body after applying the first and second aqueous yttrium-containing compositions to form a dental restoration. In one embodiment, the method comprises applying the first aqueous yttrium-containing composition to a cavity surface to penetrate the porous zirconia ceramic body. In another embodiment, the first aqueous yttrium-containing composition comprises between 5 wt % and 15 wt % yttrium-containing material and the second aqueous yttrium-containing composition comprises between 40 wt % and 65 wt % yttrium-containing component.

A sintered yttria-stabilized zirconia ceramic material in the shape of a dental restoration is provided that comprises a facial surface comprising an incisal region, a middle region, and an cervical region wherein, an yttria concentration in the incisal region at the incisal edge is greater than the yttria concentration at a distance between 0.5 mm and 5 mm from the incisal edge. In one embodiment, the incisal region comprises a metal-containing component comprising cobalt. The sintered dental restoration may have a fracture toughness between an incisal edge and to 2 mm from the incisal edge toward cervical region that increases by at least 1.5 $MPa*m^{0.5}$. The sintered dental restoration may have a change in fracture (indentation) toughness between a distance of 3.5 mm from the incisal edge to 6 mm from the incisal edge is less than 1 $MPa*m^{0.5}$. In one embodiment, the facial surface of a sintered dental restoration has an L value of at least 65, wherein the difference in CIE L values, tested according to the methods disclosed herein, between the incisal region and the cervical region is less than 1. In another embodiment, the an yttria concentration in the incisal region at the incisal edge is greater than the yttria concentration at a distance between 0.5 mm and 5 mm from the incisal edge.

A kit is provided for enhancing the translucency of a zirconia body, wherein kit comprises at least one first yttrium-containing composition comprising an aqueous solution or dispersion of at least one metallic salt as a coloring agent and approximately 5 wt % to approximately 40 wt. % yttrium salt; and at least one second yttrium-containing composition having an yttrium concentration that is higher than the first yttrium-containing composition comprising approximately 20 wt. % to approximately 70 wt. % yttrium salt, and optionally, a coloring agent, and optionally, a cobalt-containing component.

In another embodiment, a kit comprises at least two aqueous yttrium-containing compositions to apply to a porous ceramic body for enhancing optical properties in a sintered dental restoration, comprising, a first aqueous yttrium-containing composition comprising between 5 wt % and 35% wt yttrium chloride based on the total weight of the first composition, and a colorant comprising a metal-containing component as a coloring agent; and a second aqueous yttrium-containing composition comprising between 40% wt and 70 wt % yttrium chloride based on the total weight of the second composition, and optionally, a cobalt-containing component. In this embodiment, the first aqueous yttrium-containing composition or second aqueous yttrium-containing composition, or both, may further comprise an organic solvent.

Test Methods

Density

The density strongly depends on the composition and structure of the samples of the ceramic materials. Density calculations for ceramic bodies may be determined by liquid displacement method of Archimedes principle. Distilled water was used as the liquid medium. Density of ceramic samples were calculated using the following formula:

$$\rho = \frac{(W^2 - W^1)}{(W^4 - W^1) - (W^3 - W^2)}$$

ρ=Density (gram/cc);
$W_1$=Weight of empty specific gravity bottle (gram);
$W_2$=Weight of specific gravity bottle with sample (gram);
$W_3$=Weight of specific gravity bottle with sample and distill water (gram);
$W_4$=Weight of specific gravity bottle with distill water (gram).

Strength Testing

Three-point bend strength (Flexural Strength) and biaxial strength tests were conducted according to ISO 6872. Results are provided in (MPa).

Flexural Strength Test

Flexure tests were performed on sintered test materials using the Instron—Flexural Strength following ISO 6872 for preparation of strength testing for dental ceramic, flexural strength bar were milled and prepared. Once prepared, the bars were placed centrally on the bearers of the test machine so the load applied to a 4 mm wide face was along a line perpendicular to the long axis of the test piece. Then force is applied and the load needed for breaking the test piece (loading rate was 0.5 mm/min) was recorded. The flexural strength is calculated using sample's dimensional parameter and critical load information.

Flexural strength, σ, in MPa was calculated according to the following formula:

$$\sigma = \frac{3Pl}{2Wb^2}$$

where P is the breaking load, in newton; l is the test span (center-to-center distance between support rollers), in millimeters; w is the width of the specimen, i.e. the dimension of the side at right angles to the direction of the applied load, in millimeters; b is the thickness of the specimen, i.e. the dimension of the side parallel to the direction of the applied load, in millimeters. The mean and standard deviation of the strength data was reported. Means should equal or exceed the requirements.

Test bars were prepared by cutting bisque materials taking into consideration the targeted dimensions of the sintered test bars and the enlargement factor (E.F.) of the material, as follows:

starting thickness=3 mm×E.F.;

starting width=4 mm×E.F.; and starting length=55 mm×E.F.

The cut, bisque bars were sintered and flexural strength data was measured and calculated according to the 3 point flexural strength test described in ISO (International Standard) 6872 Dentistry—Ceramic Materials.

Biaxial Strength Test (Piston-on-Three-Ball Test)

Universal mechanical testing machine, capable of a crosshead speed of (1±0.5) mm/min and an ability to measure applied loads of between 10 N and 2 500 N (±1%) was used.

The Biaxial flexural strength test fixture had a sample test support of three hardened steel balls with a diameter (4.5±2 mm) positioned 120° apart on a support circle with a diameter (11±1 mm). The sample was placed concentrically on these supports and the load was applied with a flat punch with a diameter of (1.4±0.2 mm) at the center of the sample specimen.

Translucency

Translucency was measured as percent transmittance. Sample wafers were sectioned from a bisque stage block and machined to a diameter that approximates a final diameter of approximately 30 mm after sintering. Wafers were ground flat until visually free of defects with 1200 and 2000 grit SiC polishing paper. Surface dust was removed and the samples were sintered according to the sintering profile(s) described herein. The final thickness of the bisque body corresponded to a thickness of approximately 1.0 mm after sintering.

After sintering, sample wafers were briefly washed with isopropanol to remove errant surface material; however, no further surface preparation techniques were applied to the samples prior to testing. Transmission spectra were measured between the wavelengths of 360 nm to 740 nm with a Konica-Minolta CMS spectrophotometer illuminated by a D65 light source. The spectrophotometer was calibrated to white and black prior to measurement. Translucency samples were placed flush against the (approximately) 24 mm integrating sphere aperture. A minimum of four spectra were collected per sample and averaged to yield a final transmission spectra. Where noted, transmission spectra were corrected for deviations in sample thickness.

Color Space (CIE L*a*b*) Test

Zirconia materials were measured for color space according to CIE L*a*b* (International Commission on Illumination, measuring two polar axes for color, 'a' and 'b', and value (lightness, L)) values using a Konica Minolta Spectrometer with a D65 light source.

27 mm×27 mm sintered test wafers were cut from pre-sintered bisque blocks. The targeted final thickness of the test wafers after sintering was 1.0 mm. Therefore, the starting thickness for each wafer was calculated based on the targeted final thickness taking into consideration the enlargement factor (EF) as follows:

Final thickness×(EF)=bisque wafer thickness.

To measure color, the Konica Minolta Spectrometer was set on reflectance mode, and the L*a*b* values of the sample were measured. These values were referenced to materials made from traditional processes. Color equivalence is indicated if a comparison of ceramic samples made by the methods described herein and traditional methods have a ΔE of less than approximately 3 or less, approximately 2.5 or less, or approximately 2 or less.

Vickers Hardness Test

Vickers Hardness Test conditions were as follows: 19.6 N (2,000 gf) with a Load for 10 sec. Micro-indentation hardness testing was performed according to In H. Kuhn & D. Medlin (Eds.), ASM Handbook, Volume 8: Mechanical Testing and Evaluation (pp. 221-231). ASM International).

A diamond in the form of a square-based pyramid was used as the indenter shape to produce geometrically similar impressions, irrespective of size; the impression should have well-defined points of measurement; and the indenter should have high resistance to self-deformation.

Figure 8:
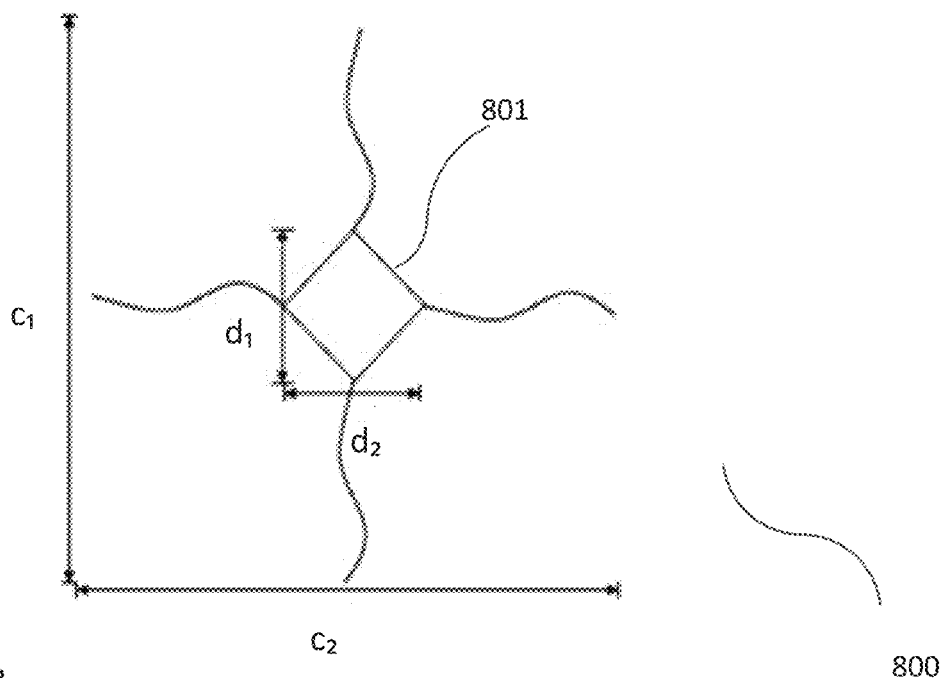
FIG. 8 is a schematic representation of Vickers Hardness indenter impression shape.

With reference to the schematic representation of a testing indentation (800) in FIG. 8, an impression (801) is observed for $d_1$=vertical indentation length; $d_2$=horizontal indentation length; $c_1$=vertical length spanned by indentation cracks; $c_2$=horizontal length spanned by indentation cracks; d=average indentation length; c=average length spanned by indentation cracks.

Hardness was calculated as: $H_{(hardness)}=1.854*P/d^2$ where P is the applied load in Newton (N) and d is the arithmetic mean of the two diagonals ($d_1$ and $d_2$) in micrometers. The hardness can then be converted into GPa as follows: H (GPa)=0.009817HV. (Ref: Vander, G. F. (2000). Micro-indentation hardness testing was performed according to In H. Kuhn & D. Medlin (Eds.), ASM Handbook, Volume 8: Mechanical Testing and Evaluation (pp. 221-231). ASM International).

Fracture Toughness from indentation method (Indentation Toughness) was calculated from the Hardness values, as follows:

$$K_{Ic} = 0.016\sqrt{\frac{E}{H}} \times \frac{P}{C^{\frac{3}{2}}}$$

where $k_{Ic}$=Fracture Toughness (MPa m$^{1/2}$); E=Young's Modulus (GPa); H=Hardness (GPa); L=load (N); and C=average crack length (m). (Ref. Evaluation of Indentation Techniques for Measuring Fracture Toughness: I, Direct Crack Measurements, J. Am. Ceram., 64(9), pp 533-538, 1981, incorporated herein by reference)

EXAMPLES

Coloring Solutions

Coloring solutions were prepared according to the coloring solutions chart, and mixed in the yttrium-containing compositions, where indicated in the Examples. Coloring solutions (1, 2 and 3) were selected that provided sintered zirconia ceramic bodies having shades that matched commonly requested shades from the Vita Classic shade guide, when applied to an unshaded, bisque body. Approximately 100 grams of a combination of terbium chloride hexahydrate and chromium chloride, and optionally, manganese sulfate were added to form a coloring solution, as described in Table 1.

TABLE 1

Coloring Solutions Chart.

| Coloring Solution No. | Coloring agent (100 grams) | Propanediol (grams) | Water (grams) | Concentration of coloring agent in solution (wt %) |
|---|---|---|---|---|
| No. 1 | TbCl$_3$, CrCl$_3$ | 429.9 | 20698 | 0.47 |
| No. 2 | TbCl$_3$, CrCl$_3$ | 449.4 | 21637 | 0.45 |
| No. 3 | TbCl$_3$, CrCl$_3$ | 214.96 | 10349 | 0.94 |
| No. 4 | MnSO$_4$, TbCl$_3$, CrCl$_3$, | 1135.18 | 57652 | 0.29 |

Examples 1-3

Pre-sintered shaded zirconia ceramic samples were treated with first and/or second yttrium-containing compositions and tested for translucency.

Sample ceramic wafers were milled from porous, pre-sintered, pre-shaded BruxZir® milling blanks (3YSZ, matching Vita Classic A2, Glidewell Laboratories, Irvine, Calif.) calculating for an enlargement factor to provide a size sinterable to a thickness of approximately 1 mm.

A first yttrium-containing composition was prepared as follows. Coloring Solution No. 2 was prepared as described in the Coloring Solutions Chart. A diluted coloring solution (33% No.2) was prepared that comprised approximately 33% by volume of the No. 2 coloring solution prepared according to the color chart above, and approximately 67% by volume of water. The first yttrium-containing composition was prepared by mixing approximately 90 wt % of the diluted (33% No. 2) coloring solution and approximately 10 wt % yttrium (III) chloride hexahydrate until the yttrium chloride dissolved.

A second yttrium-containing composition was prepared by mixing approximately 60% by weight yttrium (III) chloride hexahydrate and 0.056% by weight cobalt (II) nitrate hexahydrate (0.044 g) in 39.9% by weight 1M citric acid, until no particles were visible to the unaided eye.

Three sample ceramic wafers were treated by dipping in the first yttrium-containing compositions for less than approximately a minute and blotting to remove residual solution from the sample surface. The first yttrium-containing composition penetrated the thickness of the samples.

While still wet from the first yttrium-containing composition, the second yttrium-containing composition was brushed onto two sample ceramic wafers, as follows. For Example 1, the second yttrium-containing composition was not applied. For Example 2, a single coat of the second yttrium-containing composition was applied to the wafer (1x painted). For Example 3, three applications of the second yttrium-containing composition were applied by brushing (3xpainted), and without allowing the sample to dry between applications. All samples were sintered to approximately full theoretical density and tested for translucency and color space.

Figure 5:
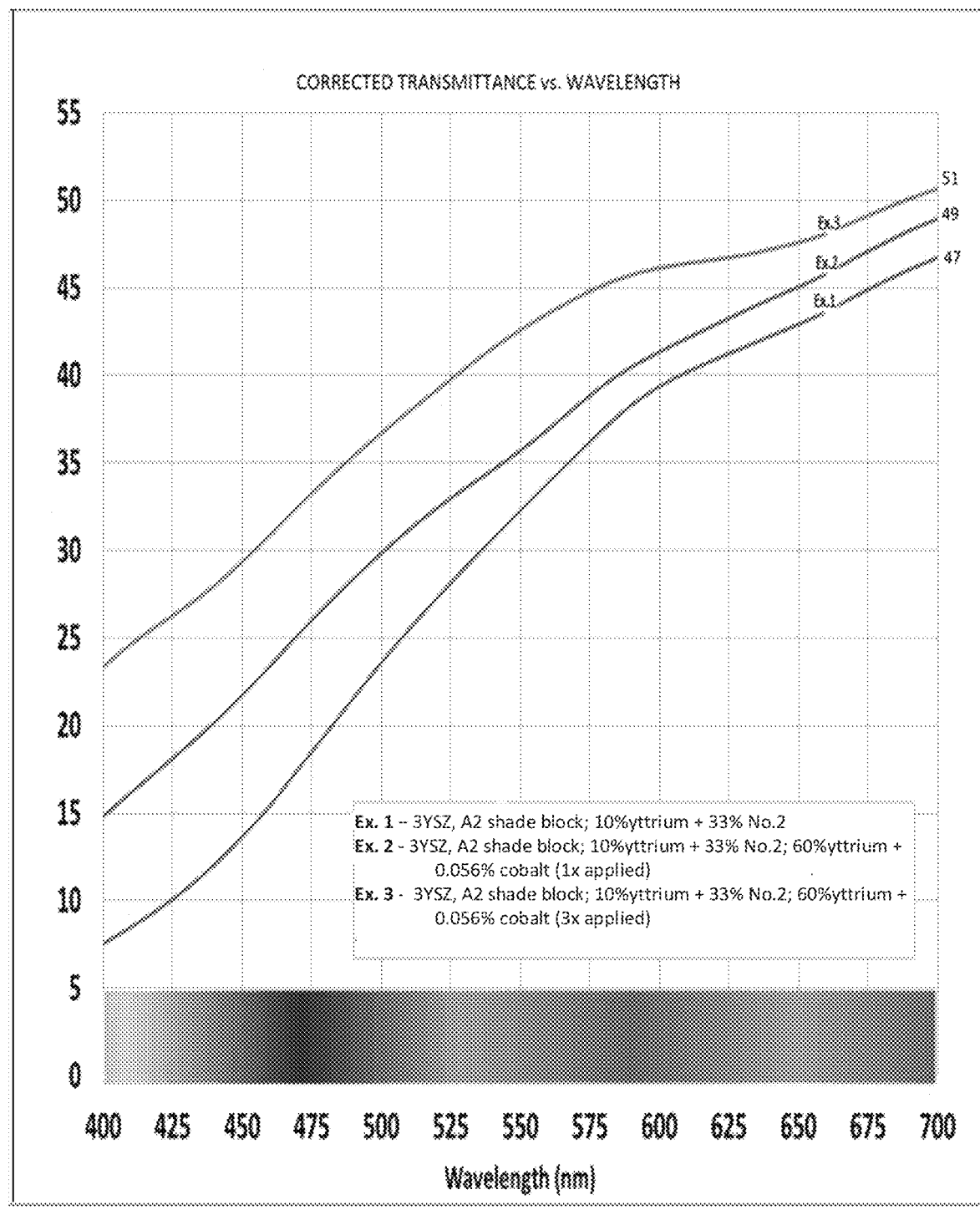
FIG. 5 is a graphical representation of transmittance measurements over a wavelength range of 400-700 nm for sintered ceramic bodies made according to disclosed methods.

Translucency was measured as percent transmittance from approximately 400 to approximately 700 nm wavelength. The results for each sample are graphically represented in FIG. 5, and corrected for sample thickness. Example 1 had approximately 47% transmittance at 700 nm. Example 2, had approximately 49% transmittance at 700 nm, and Example 3 had approximately 51% transmittance at 700 nm. Thus, Example 3 had approximately 4% transmittance greater than Example 1 at 700 nm, with an overall gain in percent transmittance at 700 nm of over 8%.

CIE L*a*b Color Space analysis results of the samples are reported in Table 2. Example 1 and Example 3 had approximately the same L (brightness) values (71.5 and 71.2, respectively), while having the greatest ΔE (11.0) among the sample comparisons.

Comparisons between Examples 1, 2, and 3 reported as Δ E are presented in Table 3. Δ E was calculated to compare L*a*b values between the three samples. A ΔF greater than 2 is deemed detectable by the unaided eye.

TABLE 2

L*a*b Values for Treated Shaded Zirconia Samples.

| Ex. # | Shade-VERIFICATION (A2 target shade) | L*(D65) | a*(D65) | b*(D65) |
|---|---|---|---|---|
| 1 | A2-shaded zirconia block; first yttrium-containing composition only | 71.53 | 1 | 14.02 |
| 2 | A2-shaded zirconia; first yttrium-containing composition + 2$^{nd}$ yttrium containing composition (1x painted) | 68.75 | 0.08 | 7.68 |
| 3 | A2-shaded zirconia body; first yttrium-containing composition + 2$^{nd}$ yttrium containing composition (3x painted) | 71.19 | 0.11 | 3.06 |

TABLE 3

L*a*b Comparison (ΔE) of Treated Shaded Zirconia Samples.

| L*a*b (Δ E) | Ex. 1 1$^{st}$ yttrium-cont. comp. only | Ex. 3 1$^{st}$ and 2$^{nd}$ (3x painted) |
|---|---|---|
| Ex. 2 1$^{st}$ and 2$^{nd}$ (1x painted) | 6.98 | 5.22 |
| Ex. 3 1$^{st}$ and 2$^{nd}$ (3x painted) | 11 | — |

Figure 6:
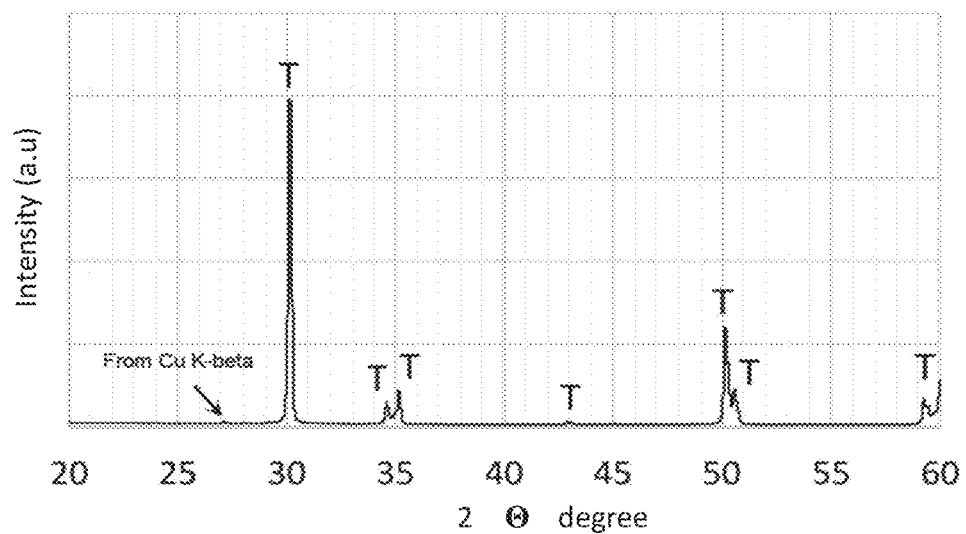
FIG. 6 and FIG. 7 are graphical representations of zirconia crystalline phases.
Figure 7:
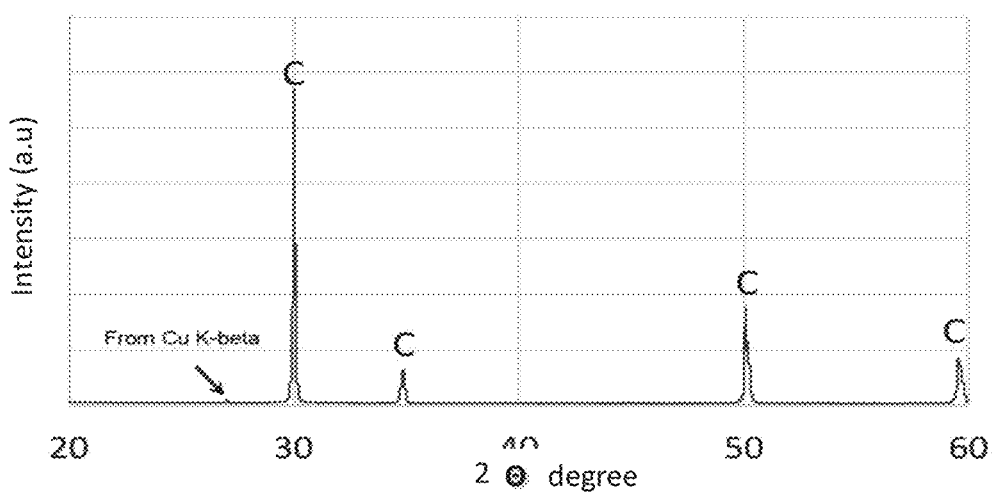

FIG. 6 and FIG. 7, illustrate graphically X-RD results showing tetragonal (T) and cubic (C) phases detected for Example 3 and Example 1, respectively, with Example 3 showing greater incidence of cubic phase.

Examples 4-5

Pre-sintered shaded zirconia ceramic samples were treated with first and/or second yttrium-containing compositions and tested for strength.

Sample bars were milled from porous, pre-sintered, pre-shaded BruxZir® milling blanks (stabilized with 3 mol % yttria-stabilized zirconia, matching Vita Classic A2, Glidewell Laboratories, Irvine, Calif.) according to the test method described above for three point bending strength. First and second yttrium-containing compositions were prepared substantially according the compositions of Examples 1-3. The first yttrium-containing composition was prepared with 10% by weight yttrium chloride and 33% No. 2 coloring solution; the second yttrium-containing composition comprised 66% by weight yttrium (III) chloride hexahydrate.

For Example 4, ten samples were prepared by applying only the first yttrium-containing composition. For Example 5, 10 samples were prepared with the first and second yttrium-containing composition, wherein prior to the first yttrium-containing composition fully drying, the second yttrium-containing compositions was applied, as follows: three overlapping applications of the second yttrium-containing composition were brushed onto the surface without fully drying between applications.

The mean break strength result of the samples of Example 4 treated with the first yttrium-containing composition alone, is provided in Table 4. The mean result of the samples of Example 5, treated with the first yttrium-containing composition and the second yttrium-containing composition, is reported in Table 4. Both techniques provided samples with break strength greater than 900 MPa.

TABLE 4

Three Point Bending Strength of Zirconia Ceramic Bodies.

| Example No. | Break Strength (MPa) |
|---|---|
| Example 4 | 1160.86 (±66) |
| Example 5 | 976.03 (±68) |

Examples 6-9

Zirconia bodies treated with yttrium-containing compositions were sintered and tested for biaxial strength.

Sample tabs were milled from porous, pre-sintered unshaded BruxZir® milling blanks (unshaded, white 3YSZ porous zirconia, stabilized with 3 mol % yttria; Glidewell Laboratories, Irvine, Calif.), according to the method described above, and sintered.

Four yttrium-containing solutions were prepared comprising yttrium-chloride and No. 1 or No. 2 colorants for a range of yttrium chloride concentrations, and applied as the first yttrium-containing composition. No. 1 or No. 2 colorant solutions were provided as described in the Colorant chart of Table 1. An amount of yttrium chloride was added to the individual colorant solutions to achieve the target weight percent for the solution, as described in Table 6. Yttrium-containing compositions were prepared comprising approximately 10 wt % yttrium chloride in No. 1 colorant solution, and 60 wt % yttrium chloride (noted as % Y in the table—based on the total weight of the treatment composition) for No. 2 colorant solutions. Yttrium chloride and colorant solutions were mixed until the yttrium chloride was dissolved, or until no more yttrium chloride was visible to the unaided eye, forming the yttrium-containing solutions.

Unshaded bisque zirconia tabs of Examples 7-9 were dipped in the yttrium-containing solutions for approximately 1 to 3 minutes and dried, according to Table 5. Unshaded bisque zirconia tab of Example 9 was dipped in a first solution comprising 10 wt % yttrium containing solutions (10 wt % yttrium chloride in No. 1 solution) and then dipped in a second yttrium-containing composition that comprised 60 wt % yttrium (III) chloride hexahydrate in 1M citric acid solution mixed until no visible particles were detected by the unaided eye. The samples were sintered to approximately full theoretical density, tested and compared to a sintered tab of unshaded zirconia having neither the first nor second yttrium-containing composition.

Example 6 was an untreated control sample. Example 7, treated with a first yttrium-containing composition having 60% by weight yttrium chloride in No. 2 solution had a biaxial strength of approximately 852 MPa, significantly lower than the untreated zirconia body of control Example 6 (approximately 1172 MPa). Example 8 and Example 9 were treated with a first yttrium-containing composition having approximately 10% by weight yttrium chloride in No. 1 solution. Example 8 had a biaxial strength of approximately 1260 MPa. Example 9 was further treated with a second yttrium-containing composition comprising approximately 60% by weight yttrium chloride in 1M citric acid. The sample tab for example 9 was positioned in the testing apparatus with the side treated with the second solution facing upward. Example 9 had a biaxial strength value of approximately 1175 MPa. Thus, Example 9, treated with both first and second yttrium chloride-containing compositions, had a biaxial strength similar to both Example 6 (untreated ceramic body), and Example 8 (treated with only a first yttrium-containing composition at 10 wt % yttrium chloride), and Example 9 had a significantly higher biaxial strength that Example 7 (treated with only a first yttrium containing composition having 60 wt % yttrium-chloride.)

TABLE 5

Strength of Zirconia Ceramic Bodies.

| Ex. No. | Zirc. 3YSZ: block shade | % Y + color in 1st Comp. | % Y in 2nd Comp. | Biaxial Strength (MPa) |
|---|---|---|---|---|
| 6 | unshaded, white | — | — | 1172 (±205) |
| 7 | unshaded, white | 60% Y + No. 2 | — | 852 (±91) |
| 8 | unshaded, white | 10% Y + No. 1 | — | 1260 (±63) |
| 9 | unshaded, white | 10% Y + No. 1 | 60% Y | 1175 (±163) |

Examples 10-16

Zirconia ceramic bodies treated with yttrium-containing compositions were sintered and tested for strength.

Sample wafers were milled from porous, pre-sintered shaded BruxZir® milling blanks (Shade 100 zirconia mill blanks, stabilized with 3 mol % yttria; Glidewell Laboratories, Irvine, Calif.) to a thickness of approximately 1 mm. The samples wafers were either left untreated, or treated with only a first yttrium-containing composition, or treated with both a first and second yttrium-containing composition.

The first yttrium-containing compositions comprised No. 1 or No. 2 colorant solutions and 10 wt % yttrium chloride, according to the description in Table 6. No. 1 or No. 2 colorant solutions were provided as described in Table 1. To form the yttrium-containing treatment compositions having 10 wt % yttrium chloride (based on the total weight of the treatment composition) and No. 1 or No. 2, approximately 10 wt % yttrium chloride was mixed into 90 wt % of the colorant solution (No. 1 or No. 2) until dissolved, or until no more yttrium chloride was visible to the unaided eye.

To form the first yttrium-containing treatment compositions having 10 wt % yttrium chloride and ⅓ No. 1, No. 1 colorant solutions were diluted in water to a weight percent of approximately 33 wt % No. 1 and 67 wt % water. Approximately 10 wt % yttrium chloride was mixed in the dilute No. 1 solution, until dissolved, or until no more yttrium chloride was visible to the unaided eye.

A second yttrium containing composition was formed by mixing approximately 60 wt % yttrium chloride in 40 wt % 1M citric acid until dissolved, or until more particles were visible to the unaided eye.

Pre-shaded bisque zirconia wafers were dipped in the first yttrium-containing treatment compositions for approximately 1 to 3 minutes. Several samples were further treated with a second yttrium-containing composition according to Table 6. The samples were dried and sintered to approximately full theoretical density. Samples were measured for 3 Point Bend Strength and Biaxial Strength. Sample strengths were compared to wafers of untreated shaded zirconia (Shade 100) that were not dipped in a treatment composition.

TABLE 6

Strength of Zirconia Ceramic Bodies.

| Ex. No. | Zirc 3YSZ: block shade | % Y + colorant - 1st yttrium Composition | % Y - 2nd yttrium Composition | 3-Point Bending Strength (MPa) | Biaxial Strength (MPa) |
|---|---|---|---|---|---|
| 10 | shade 100 | — | — | 1186(±50) | 1429(±136) |
| 11 | shade 100 | 10% Y + ⅓ No.1 | — | 1039(±85) | 1330(±85) |
| 12 | shade 100 | 10% Y + ⅓ No.1 | 60% Y | 1008(±19) | 1335(±98) |
| 13 | shade 100 | 10% Y + No.1 | — | 1179(±77) | 1238(±19) |
| 14 | shade 100 | 10% Y + No.1 | 60% Y | 1208(±74) | 1078(±127) |
| 15 | shade 100 | 10% Y + No.2 | — | 1062(±60) | 1242(±115) |
| 16 | shade 100 | 10% Y + No.2 | 60% Y | 1143(±63) | 1349(±99) |

All samples had three point bend strength and biaxial strength values that exceeded 1000 MPa. Thus, samples treated with a first composition comprising yttrium chloride and second yttrium-containing composition having approximately 60 wt. % yttrium chloride had strength values greater than 1000 MPa for both three point bend and biaxial strength.

Examples 17-32

Zirconia ceramic bodies treated with yttrium-containing compositions were sintered and inspected for visible cracking.

Sample wafers were milled from porous, pre-sintered shaded and unshaded BruxZir® milling blanks (Shade 100 and Shade 200 zirconia mill blanks, and unshaded zirconia mill blanks, 3YSZ; Glidewell Laboratories, Irvine, Calif.) to a thickness of approximately 1 mm. The samples wafers were with both first and second yttrium-containing compositions.

The first yttrium-containing compositions were prepared comprising no coloring solutions, or No. 1, 33% No. 1, No. 2, or No. 4, colorant solution as prepared above (Colorant Chart). The first yttrium-containing compositions further comprised yttrium chloride in a range of approximately 10 wt % to 50 wt % according to Table 7. Yttrium chloride was dissolved in the coloring solution, or in water where no coloring solution was used.

The second yttrium-containing compositions prepared by mixing approximately 60 wt % yttrium chloride hexahydrate, and 0.0125 wt % copper (II) chloride dihydrate until more particles were visible to the unaided eye.

Pre-sintered bisque zirconia wafers were dipped in the first yttrium-containing treatment compositions for approximately 1 minute. Dipped wafers were treated with the second yttrium-containing composition according to Table 7. The samples were dried and sintered to approximately full theoretical density. Wafer samples were visibly inspected for cracking by a technician with unaided eye, reported in Table 7.

TABLE 7

Inspection of Sintered Ceramic Bodies Treated with First and Second Yttrium-Containing Compositions for Crack For Visible Formation.

| Example No. | Zirc 3YSZ: block shade | First yttrium Composition* | Second yttrium Composition | Visible Cracks |
|---|---|---|---|---|
| 17 | Unshaded | 30 wt. % Y; | 60 wt. % Y | yes |
| 18 | | 50 wt. % Y | | yes |
| 19 | Unshaded | 10 wt. % Y + No.1; | 60 wt. % Y | no |
| 20 | | 10 wt. % Y + No.2 | | no |
| 21 | Unshaded | 30 wt. % Y + No.2; | 60 wt. % Y | no |
| 22 | | 30 wt. % Y + No.4 | | no |
| 23 | Shade 100 | 30 wt. % Y; | 60 wt. % Y | yes |
| 24 | | 50 wt. % Y | | yes |
| 25 | Shade 100 | 10 wt. % Y + 33% No.1; | 60 wt. % Y | no |
| 26 | | 30 wt. % Y + No.2 | | no |
| 27 | Shade 200 | 30 wt. % Y; | 60 wt. % Y | yes |
| 28 | | 50 wt. % Y | | yes |
| 29 | Shade 200 | 30 wt. % Y; | 60 wt. % Y + | yes |
| 30 | | 50 wt. % Y | Cu | yes |
| 31 | Shade 200 | 10 wt. % Y + No.2; | 60 wt. % Y | no |
| 32 | | 20 wt. % Y + No.2 | | no |

*Y = yttrium chloride hexahydrate

Examples 17-18, 23-24, and 27-30, having no colorant in the first yttrium-containing compositions showed visible crack formation after sintering the zirconia ceramic bodies.

Examples 19-22, 25-26, and 31-32, having at least a dilute coloring solution in the first yttrium-containing composition formed no visibly detectable cracks.

Example 33

A zirconia dental restoration was treated according to the described methods and tested for hardness and fracture toughness (by indentation method).

A ceramic body was milled into the form of a dental restoration crown from a porous, shaded zirconia blank (pre-sintered, bisque shade A2, 3YSZ). First and second yttrium-containing compositions were prepared as described in Examples 1-3, except the second yttrium-containing composition contained approximately 66 wt. % yttrium chloride hexahydrate and 0.08 wt. % cobalt nitrate in solution in 1M citric acid solution, and the second yttrium-containing composition, was painted on the dental form by stroking 5 times after application of the first yttrium-containing composition. After drying, the sample was sintered to full density and tested.

Figure 9:
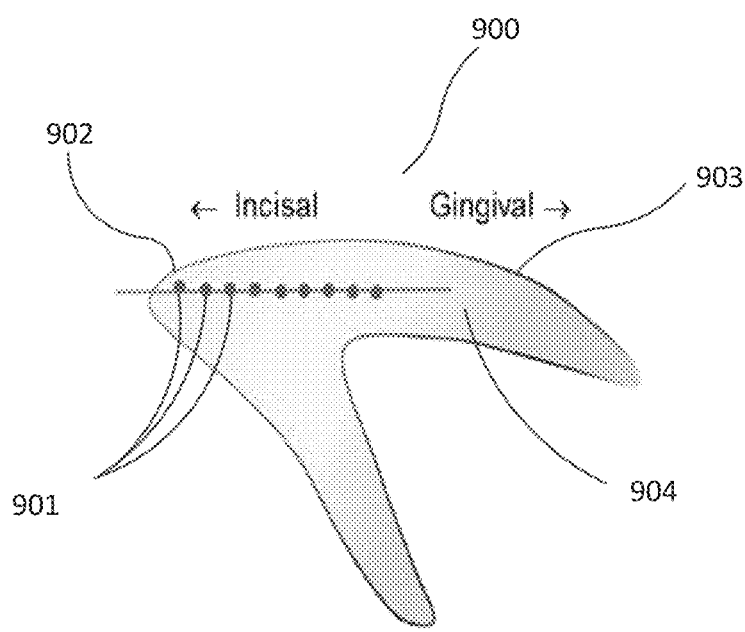
FIG. 9 is an illustration of a cross-sectional representation of a crown test sample for hardness testing.
Figure 10:
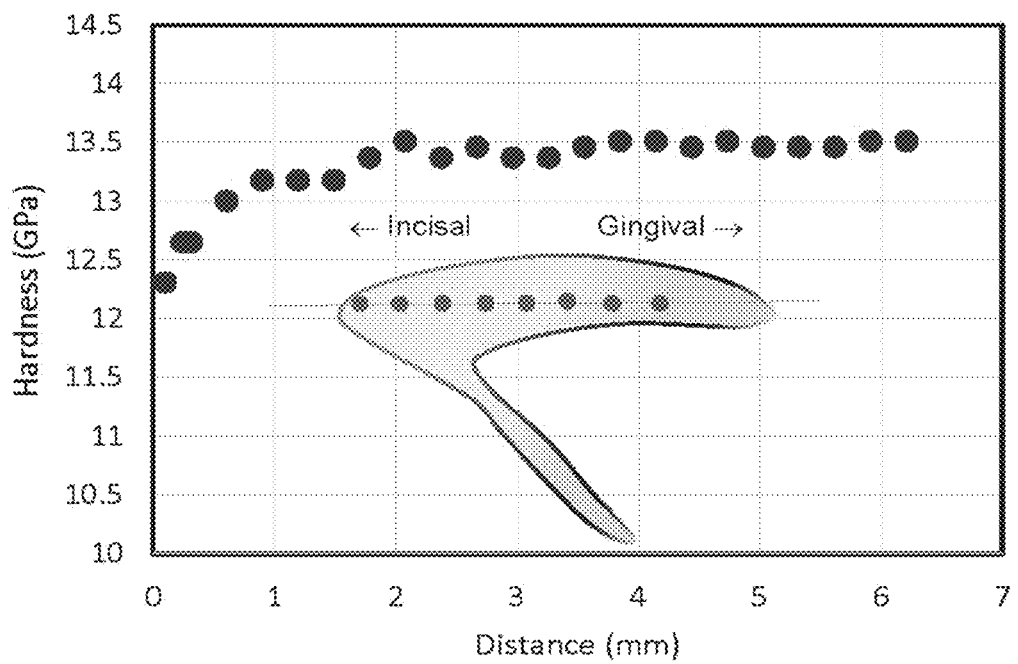
FIG. 10 and FIG. 11 are graphical representations of Hardness and Fracture Toughness results for one embodiment of a zirconia crown.
Figure 11:
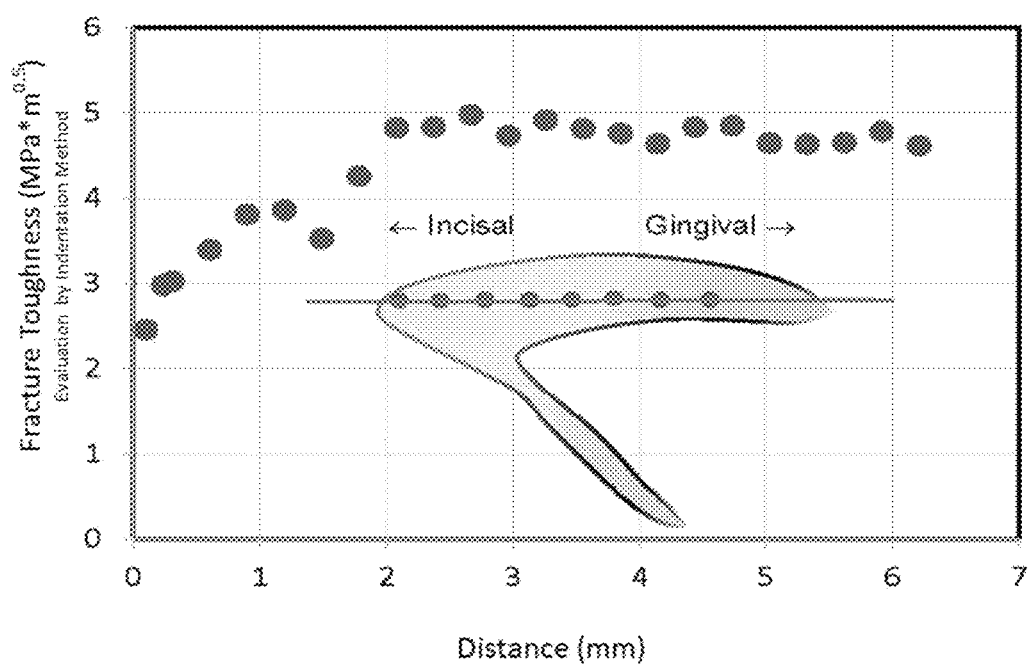

A cross-sectional area of the sample was prepared and tested for hardness, and calculated for toughness according to the test procedures described herein. FIG. 8 is a schematic representation of a Vickers indenter shape for use in the method described herein. FIG. 9, for illustrative purposes only and not necessarily to scale, is a cross-sectional representation of a dental crown (900) depicting hardness testing at multiple points (for example, 901) from the incisal edge (902) in the apical direction toward the margin area (903). FIG. 11 graphically represents fracture toughness results at testing increments on the crown test sample. FIG. 11 shows a gradual increase in fracture toughness as the distance from the incisal edge (distance=0 mm) increases in the apical direction to the cervical region (distance=~10 mm). FIG. 10 graphically represents hardness gradient that results at testing increments for the zirconia crown, and shows increasing hardness values as distance from the incisal edge (~0 mm) increases for a distance of about 3 mm. Results are reported in Table 8.

TABLE 8

Hardness and Toughness Values for Zirconia Restoration Samples.

| Distance from incisal to gingival (mm) | Hardness (GPa) | Indentation Toughness (MPa*m$^{0.5}$) |
|---|---|---|
| 0.10 | 12.31 | 2.45 |
| 0.24 | 12.65 | 2.98 |
| 0.31 | 12.65 | 3.02 |
| 0.61 | 13.00 | 3.39 |
| 0.90 | 13.18 | 3.80 |
| 1.20 | 13.18 | 3.85 |
| 1.49 | 13.18 | 3.52 |
| 1.79 | 13.37 | 4.25 |
| 2.08 | 13.51 | 4.82 |
| 2.38 | 13.37 | 4.83 |
| 2.67 | 13.46 | 4.97 |
| 2.97 | 13.37 | 4.73 |
| 3.26 | 13.37 | 4.91 |
| 3.56 | 13.46 | 4.81 |
| 3.85 | 13.51 | 4.76 |
| 4.15 | 13.51 | 4.64 |
| 4.44 | 13.46 | 4.83 |
| 4.74 | 13.51 | 4.85 |
| 5.03 | 13.46 | 4.64 |
| 5.33 | 13.46 | 4.63 |
| 5.62 | 13.46 | 4.65 |
| 5.92 | 13.51 | 4.78 |
| 6.21 | 13.51 | 4.61 |

The results show hardness and indentation toughness increasing as the distance (mm) from the incisal edge increases.

Examples 34-37

Zirconia samples were prepared by the methods disclosed to obtain bleached shade restorations that correspond to Vita Classical bleach shades BL1, BL2, BL3 and BL4.

Three zirconia restorations were milled from unshaded, bisque 3YSZ zirconia blocks, then treated with first and second yttria-containing compositions as follows. A first yttrium-containing composition, prepared as described in Example 1 using the coloring solutions No. 2, for Example 34, and No.3 for Examples 36-37, and containing approximately 10 wt % yttrium (III) chloride hexahydrate. The second yttrium-containing composition was prepared by mixing approximately 66% by weight yttrium chloride and approximately 0.02% by weight cobalt (II) nitrate hexahydrate (0.044 g) and 39.9% by weight 1M citric acid, until no particles were visible to the unaided eye.

The first yttrium containing composition was brushed on to the entire surface of the bisque ceramic restoration body in a two or more painting applications in accordance with Table 9. Before the first yttrium-containing composition fully dried, the second yttrium-containing composition was brushed on the incisal portion of the restoration in approximately 4 painting applications that varied in total distance from incisal edge. For example, a first painting application covered approximately 45% of the tooth surface from the incisal edge toward the middle of the buccal tooth surface, or approximately 5-6 mm from incisal edge; a third application cover approximately 3-4 mm from incisal edge; a third application covered approximately 2-3 mm from incisal edge; and, a fourth painting application covered a distance of approximately 1-2 mm from incisal edge, using the pattern illustrated in FIG. 1) without drying between applications.

TABLE 9

First Yttrium-containing Composition for Bleach Shade Restorations.

| Example No. | Vita Classical Bleach shade | % Y + color for 1$^{st}$ Yttrium-containing Comp. | Number of Painting |
|---|---|---|---|
| 34 | BL1 | 10 wt % Yttrium salt with 33 wt % No.2 coloring solution | 2 |
| 35 | BL2 | 10 wt % Yttrium salt with 33 wt % No.3 coloring solution | 2 |
| 36 | BL3 | 10 wt % Yttrium salt with 33 wt % No.3 coloring solution | 3 |
| 37 | BL4 | 10 wt % Yttrium salt with 33 wt % No.3 coloring solution | 5 |

The treated bodies were allowed to dry at ambient conditions and then sintered according to Example 1, to approximately full density. A visual analysis by a laboratory technician determined that the resulting samples had no cracks, and had an enamel appearance with shades that matched Vita Classical bleach shades, as provided above in Table 9.

Example 38-39

Samples of unshaded bisque zirconia ceramic bodies were prepared and treated with an yttrium-containing composition comprising 66% wt yttrium (III) chloride hexahydrate with and without the addition of 0.05% cobalt nitrate, the balance 1M citric acid aqueous solution.

Unshaded 3YSZ zirconia ceramic bodies were prepared as bisque samples and treated with an yttrium-containing composition with or without cobalt nitrate. The samples were dried, sintered to full density and tested for Color Space—CIE L*a*b values according to the method provided herein.

TABLE 10

Zirconia Ceramic Treated with Yttrium-containing Composition with and without Cobalt.

| Material system | L*(D65) | a*(D65) | B*(D65) |
| --- | --- | --- | --- |
| Control - unshaded zirconia ceramic | 79.3 | −0.9 | −1.8 |
| Ex. 38. With cobalt | 75.3 | −1.2 | −2.8 |
| Ex. 39. Without cobalt | 75.8 | −0.7 | −2.5 |

Table 10 shows that a sample treated with an yttrium-containing composition comprising cobalt nitrate and yttrium salt showed a shift in a* value (comparing a* value of the control), while obtaining substantially similar shift in the b* value (in the blue direction) and L value as the sample prepared without cobalt.

Examples 40-41

Pre-sintered zirconia ceramic samples were treated with first and/or second yttrium-containing compositions and tested for strength.

Sample bars were milled from porous, pre-sintered, BruxZir® HT white milling blanks (3 YS, Glidewell Laboratories, Irvine, Calif.) according to the test method described above for three point bending strength. First and second yttrium-containing compositions were prepared substantially according the compositions of Examples 1-3. The first yttrium-containing composition was prepared with 10% by weight yttrium chloride in a 33% dilution of No.4 coloring solution; the second yttrium-containing composition comprised 66% by weight yttrium (III) chloride hexahydrate with the addition of 0.05% by weight of cobalt nitrate with 1M citric acid solution.

For Example 40, six samples were prepared by applying only the first yttrium-containing composition drop-wise on the ceramic sample. For Example 41, six samples were prepared by applying the first yttrium-containing solution drop-wise, and applying the second yttrium-containing composition by brushing 3 applications prior to the first yttrium-containing composition fully drying. The samples were sintered to approximately full theoretical density and tested for strength.

TABLE 11

Three Point Bending Strength of Zirconia Ceramic Bodies.

| Example No. | Break Strength (MPa) |
| --- | --- |
| Example 40 | 1012 (±86) |
| Example 41 | 941 (±21) |

The mean results of the samples is reported in Table 11. Both techniques provided samples with break strength greater than 900 MPa.

We claim:

1. A sintered zirconia ceramic dental restoration comprising
   a sintered zirconia ceramic body comprising an yttria-stabilized zirconia ceramic material comprising 2 mol % yttria to 5 mol % yttria, having a dental restoration shape comprising an incisal edge and a cervical region,
   wherein the sintered zirconia ceramic body exhibits an indentation toughness gradient in an incisal region, wherein an indentation toughness increases by at least 1.5 MPa*$m^{0.5}$ from the incisal edge to a distance of 3 mm from the incisal edge, toward the cervical region.

2. The sintered zirconia ceramic dental restoration of claim 1, wherein the indentation toughness increases by at least 2MPa*$m^{0.5}$.

3. The method of claim 1, wherein the incisal region comprises cobalt.

4. The method of claim 1, wherein the sintered zirconia ceramic body comprises a cervical region and a middle region that is between the incisal region and the cervical region, wherein an indentation toughness difference between the middle region and the cervical region is less than 1 MPa*$m^{0.5}$.

* * * * *